United States Patent [19]

Ackermann et al.

[11] Patent Number: 4,618,615

[45] Date of Patent: Oct. 21, 1986

[54] CERTAIN 6-PHENOXY-2-PYRIDINYL-α-METHYL-METHYLENE ESTERS OF α-CYCLOPROPYL-α-PHENYL-ACETIC ACID DERIVATIVES AND THEIR USE FOR CONTROLLING PESTS

[75] Inventors: Peter Ackermann, Pfeffingen; Laurenz Gsell, Basel; Boris Kohler, Binningen, all of Switzerland

[73] Assignee: Ciba-Geigy Corporation, Ardsley, N.Y.

[21] Appl. No.: 549,149

[22] Filed: Nov. 7, 1983

[30] Foreign Application Priority Data

Nov. 18, 1982 [CH] Switzerland ............ 6727/82
Sep. 1, 1983 [CH] Switzerland ............ 4816/83

[51] Int. Cl.[4] ............ C07D 213/64; C07D 491/056; A01N 43/40
[52] U.S. Cl. ............ 514/338; 514/345; 514/351; 546/270; 546/300; 546/302
[58] Field of Search ............ 546/300, 302, 270; 424/263; 514/351, 345, 338

[56] References Cited

U.S. PATENT DOCUMENTS 4,163,787  8/1979  Malhotra et al. ............ 424/263
4,228,172 10/1980  Malhotra et al. ............ 424/263
4,262,001  4/1981  Malhotra et al. ............ 424/263

FOREIGN PATENT DOCUMENTS 0076961  4/1983  European Pat. Off. ............ 546/302

OTHER PUBLICATIONS

Elliott et al., Chem. Abstracts, vol. 94, (25), Abst. No. 208,489q, Jun. 22, 1981.
Chem. Abstracts, vol. 95, (9), Abst. No. 75,482d, Aug. 31, 1981.

*Primary Examiner*—Alan L. Rotman
*Attorney, Agent, or Firm*—Edward McC. Roberts; Kevin T. Mansfield

[57] ABSTRACT

α-Cyclopropyl-α-phenylacetate and salts thereof, corresponding to the formula

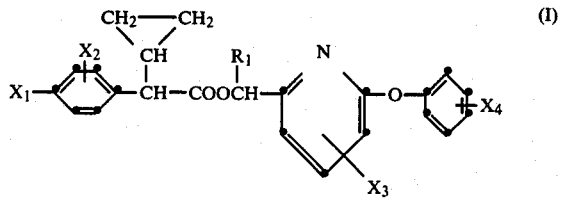

wherein
$R_1$ is hydrogen, methyl, cyano or ethinyl,
$X_1$ is hydrogen, halogen, $C_1$-$C_5$-alkyl, $C_1$-$C_5$-haloalkyl or $C_1$-$C_5$-alkoxy,
$X_2$ is hydrogen, halogen or $C_1$-$C_5$-alkyl, or together with $X_1$ is methylenedioxy, and
$X_3$ and $X_4$ are hydrogen or halogen.

Processes for producing these α-cyclopropyl-α-phenylacetates and their use for controlling pests are described.

6 Claims, No Drawings

CERTAIN 6-PHENOXY-2-PYRIDINYL-α-METHYL-METHYLENE ESTERS OF α-CYCLOPROPYL-α-PHENYL-ACETIC ACID DERIVATIVES AND THEIR USE FOR CONTROLLING PESTS

The present invention relates to α-cyclopropyl-α-phenylacetates and salts thereof, to processes for producing them, and to their use for controlling pests.

The α-cyclopropyl-α-phenylacetates correspond to the formula

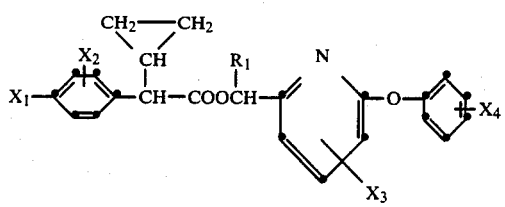

(I)

wherein $R_1$ is hydrogen, methyl, cyano or ethinyl, $X_1$ is hydrogen, halogen, $C_1$-$C_5$-alkyl, $C_1$-$C_5$-haloalkyl or $C_1$-$C_5$-alkoxy, $X_2$ is hydrogen, halogen or $C_1$-$C_5$-alkyl, or together with $X_1$ is methylenedioxy, and $X_3$ and $X_4$ are each hydrogen or halogen.

Suitable for forming salts are inorganic acids, for example HCl, $H_2SO_4$, HBr and $H_3PO_4$; and organic acids, for example: saturated and unsaturated mono-, di- and tricarboxylic acids, for example formic acid, acetic acid, oxalic acid, phthalic acid, succinic acid and citric acid.

Halogen in this case is fluorine, chlorine, bromine or iodine.

The alkyl, haloalkyl and alkoxy groups denoted by $X_1$ and $X_2$ can be straight-chain or branched-chain. Examples of such groups are, inter alia: methyl, trifluoromethyl, methoxy, ethyl, ethoxy, propyl, isopropyl, n-butyl and n-pentyl.

Particularly preferred compounds of the formula I are those wherein $R_1$ is hydrogen, methyl, cyano or ethinyl, $X_1$ is halogen, $X_2$ and $X_3$ are each hydrogen, and $X_4$ is hydrogen or halogen.

More especially preferred are compounds of the formula I wherein $R_1$ is methyl, cyano or ethinyl, $X_1$ is chlorine, $X_2$ and $X_3$ are each hydrogen, and $X_4$ is hydrogen or halogen.

The compounds of the formula I are produced by methods known per se, for example as follows:

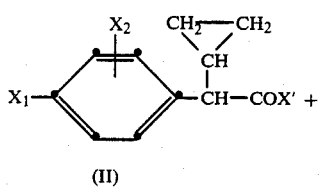

(II)

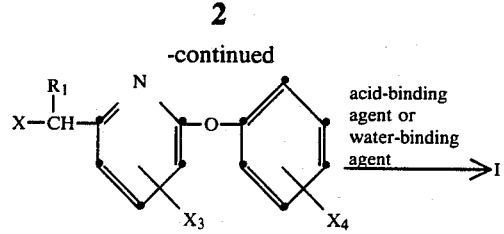

(III)

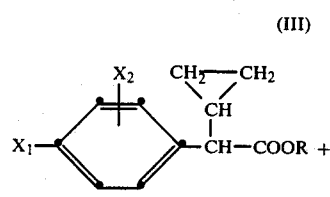

(IV)

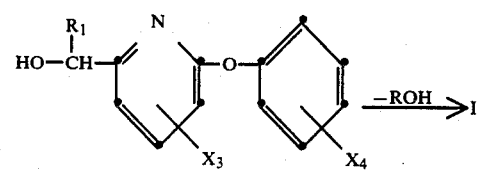

(V)

In the formulae II to V, the symbols $R_1$, $X_1$, $X_2$, $X_3$ and $X_4$ have the meanings defined under the formula I.

In the formulae II and III, one of the symbols X and X' us a hydroxyl group and the other is a halogen atom, particularly chlorine or bromine, or both symbols are a hydroxyl group, and in the formula IV, R is hydrogen or $C_1$-$C_4$-alkyl, especially methyl or ethyl. Acid-binding agents are in particular: tertiary amines, such as trialkylamines and pyridine, also hydroxides, oxides, carbonates and bicarbonates of alkali metals and alkaline-earth metals, as well as alkali metal alcoholates, for example potassium tert-butylate and sodium methylate. The water-binding agent used can be for example dicyclohexylcarbodiimide. The processes 1 and 2 are performed at a reaction temperature of between −10° and 120° C., usually between 20° and 80° C., under normal or elevated pressure, and preferably in an inert solvent or diluent. Suitable solvents or diluents are for example: ethers and ethereal compounds, such as diethyl ether, dipropyl ether, dioxane, dimethoxyethane and tetrahydrofuran; amides, such as N,N-dialkylated carboxylic acid amides; aliphatic, aromatic as well as halogenated hydrocarbons, especially benzene, toluene, xylenes, chloroform and chlorobenzene; nitriles such as acetonitrile; dimethyl sulfoxide, and ketones such as acetone and methyl ethyl ketone.

The starting materials of the formulae II to V are known, or they can be produced by methods analogous to known methods.

If homogeneous optically active starting materials are not used in producing the compounds of the formula I, these compounds are obtained as mixtures of various optically active isomers. The different isomeric mixtures can be separated by known methods into the individual isomers. By the term 'compounds of the formula I' are meant both the individual isomers and the mixtures thereof.

The compounds of the formula I are suitable for controlling various pests on animals and plants. They can thus be used for controlling insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also mites and ticks of the order Acarina.

In particular, compounds of the formula I are suitable for controlling insects that damage plants, especially insects that damage plants by eating, in crops of ornamental plants and productive plants, particularly in cotton and rice crops (for example against Spodoptera littoralis, Heliothis virescens, Chilo suppressalis and Laodelphax), and in vegetable and fruit crops (for example against Leptinotarsa decemlineata, Myzus persicae, Laspeyresia pomonella and Adoxophyes reticulana), and also for controlling soil insects (for example Aulacophora femoralis, Chortophila brassicae, Diabrotica balteata, Pachnoda savigni and Scotia ypsilon).

Active substances of the formula I have a very favourable action also against flies, for example Musca domestica, and against mosquito larvae.

The acaricidal and insecticidal action can be substantially broadened and adapted to suit the given circumstances by the addition of other insecticides and/or acaricides. Suitable additives are for example: organic phosphorus compounds, nitrophenols and derivatives thereof, formamidines, ureas, other pyrethrin-like compounds, as well as carbamates and chlorinated hydrocarbons.

Compounds of the formula I are combined particularly advantageously also with substances having a synergistic or intensifying effect on pyrethroids. Examples of compounds of this type are, inter alia: piperonylbutoxide, propynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-octylsulfinyl)-propyl)-benzene.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid, or of a naphthalenesulfonic acid-formaldehyde condensation product. Also suitable are corresponding phosphates, for example salts of the phosphoric ester of a p-nonylphenol-(4-14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyl-trimethylammonium chloride or benzyldi(2-chloroethyl)ethylammonium bromide.

The tensides customarily used in formulation practice are described, inter alia, in the following publications:

"McCutcheon's Detergents and Emulsifiers Annual", MC Publishing Corp., Ringwood, N.J., 1979; and Dr. Helmut Stache "Tensid Taschenbuch", Carl Hauser Verlag, Munich/Vienna, 1981.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25% of a tenside.

Whereas commercial products are preferably in the form of concentrated compositions, the compositions employed by the end-user are as a rule diluted.

The compositions can also contain further additives such as stabilisers, antifoam agents, viscosity regulators, binders and adhesives, as well as fertilisers or other active ingredients for obtaining special effects.

Formulation examples for liquid active ingredients of the formula I (%=percent by weight)

| 1. Emulsion concentrates | (a) | (b) | (c) |
| --- | --- | --- | --- |
| active ingredient | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 2. Solutions | (a) | (b) | (c) | (d) |
| --- | --- | --- | --- | --- |
| active ingredient | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160-190° C.) | — | — | 94% | — |

These solutions are suitable for application in the form of very small drops.

| 3. Granulates | (a) | (b) |
| --- | --- | --- |
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 4. Dusts | (a) | (b) |
| --- | --- | --- |
| active ingredient | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation examples for solid active ingredients of the formula I (%=percent by weight)

| 5. Wettable powders | (a) | (b) | (c) |
| --- | --- | --- | --- |
| active ingredient | 20% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7-8 mols of ethylene oxide) | — | 2% | — |
| highly dispersed silicic acid | 5% | 10% | 10% |
| kaolin | 67% | 27% | — |

The active ingredient is well mixed with the additives and the mixture is thoroughly ground in a suitable mill. Wettable powders which can be diluted with water to give suspensions of the required concentration are obtained.

| 6. Emulsion concentrate | |
| --- | --- |
| active ingredient | 10% |
| octylphenol polyethylene glycol ether (4-5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 7. Dusts | (a) | (b) |
| --- | --- | --- |
| active ingredient | 5% | 8% |
| talcum | 95% | — |
| kaolin | — | 92% |

Dusts ready for use are obtained by mixing the active ingredient with the carrier, and grinding the mixture in a suitable mill.

| 8. Extruder granulate | |
| --- | --- |
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded and then dried in a stream of air.

| 9. Coated granulate | |
| --- | --- |
| active ingredient | 3% |

-continued

| 9. Coated granulate | |
|---|---|
| polyethylene glycol (M.W. 200) | 3% |
| kaolin | 94% |

The finely ground active ingredient is evenly applied, in a mixer, to the kaolin moistened with polyethylene glycol. Dustfree coated granulates are obtained in this manner.

| 10. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentration required.

EXAMPLE 1

Production of α-cyclopropyl-α-(p-chlorophenyl)-cyano-(6-phenoxy-2-pyridinyl)-methyl acetate There are added successively dropwise at 0° C. to 5 g of the compound of the formula

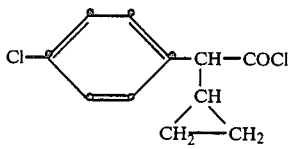

in 50 ml of toluene, 1.5 ml of pyridine and 5 g of the compound of the formula

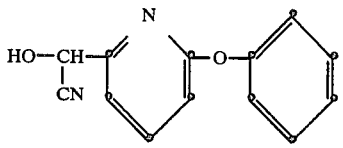

in 100 ml of toluene/ether (1:1). The reaction mixture is stirred for 30 hours at 25° C.; it is subsequently poured into 2N hydrochloric acid and extracted with ether. The ether phase is washed with saturated sodium bicarbonate and sodium chloride solution, dried over magnesium sulfate and concentrated by evaporation. The product is chromatographed through silica gel with toluene/ethyl acetate (95:5) as the eluant to thus obtain the compound No. 1 of the formula

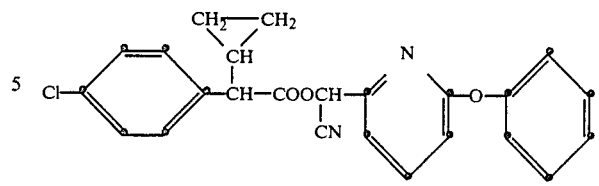

having a refractive index of $n_D^{20°} = 1.5753$.

The following compounds are produced in an analogous manner:

| No. | $R_1$ | $X'$ | Physical data |
|---|---|---|---|
| 2 | —C≡CH | H | $n_D^{20°} = 1.5717$ |
| 3 | —CN | Br | $n_D^{40°} = 1.5825$ |
| 4 | —CN | I | $n_D^{40°} = 1.5952$ |
| 5 | H | H | $n_D^{20°} = 1.5827$ |
| 6 | —CH$_3$ | H | $n_D^{20°} = 1.5735$ |
| 7 | H | Br | $n_D^{20°} = 1.5948$ |
| 8 | —C≡CH | Br | $n_D^{20°} = 1.5916$ |
| 9 | —CH$_3$ | Br | $n_D^{20°} = 1.5855$ |
| 10 | H | I | $n_D^{20°} = 1.6138$ |
| 11 | —CH$_3$ | I | $n_D^{20°} = 1.6022$ |
| 12 | H | Cl | $n_D^{23°} = 1.5921$ |
| 13 | —CN | Cl | $n_D^{23°} = 1.5829$ |

EXAMPLE 2

Insecticidal stomach-poison action: Spodoptera littoralis

Cotton plants are sprayed with a test solution containing 50, 100 and 200 ppm, respectively, of the compound to be tested. After the drying of the coating, larvae of Spodoptera littoralis (L$_3$ stage) are settled onto the plants. Two plants are used per test compound and per concentration, and an assessment of the mortality rate achieved is made after 2, 4, 24 and 48 hours. The test is carried out at 28° C. with 60% relative humidity.

Compounds according to Example 1 exhibit in the above test against Spodoptera littoralis the levels of activity listed in the following Table.

Biological test results

The Table which follows shows the test results on the basis of the Example given in the foregoing, the evaluation index with regard to the percentage mortality rate being as follows:

A: 70–100% mortality at 50 ppm active-ingredient concentration
B: 70–100% mortality at 100 ppm active-ingredient concentration
C: 70–100% mortality at 200 ppm active-ingredient concentration.

| Compound No. | Effectiveness against Spodoptera littoralis larvae |
|---|---|
| 1 | B |
| 2 | B |
| 3 | A |
| 4 | A |
| 5 | A |
| 6 | A |
| 7 | B |
| 8 | A |
| 9 | A |

| -continued | |
|---|---|
| 10 | A |
| 11 | A |
| 12 | B |
| 13 | A |

EXAMPLE 3

Action against Diabrotica balteata 750 ml of compost soil are mixed with 150 ml of test solution containing 3, 0.75, 0.2 and 0.05 ppm, respectively, of active ingredient. Maize seedlings are potted with the treated soil in plastic pots (4 seedlings per pot of 10 cm diameter). The pots are immediately afterwards infested in each case with 10 L₃ larvae of Diabrotica balteata, and an assessment of the results obtained is made 10 days after the larvae were placed into the pots. In the case where the first examination shows a mortality rate of 80–100%, the same soil sample with 4 fresh maize seedlings is again infested with 10 larvae.

Compounds according to Example 1 exhibit in the above test a 100% action against L₃ larvae of Diabrotica balteata.

What is claimed is:

1. An α-cyclopropyl-α-phenylacetate or salt thereof, of the formula

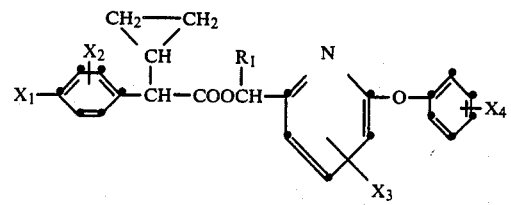

wherein
$R_1$ is methyl,
$X_1$ is hydrogen, halogen, $C_1$–$C_5$-alkyl, $C_1$–$C_5$-haloalkyl or $C_1$–$C_5$-alkoxy,
$X_2$ is hydrogen, halogen or $C_1$–$C_5$-alkyl, or together with $X_1$ is methylenedioxy, and
$X_3$ and $X_4$ are each hydrogen or halogen.

2. A compound of claim 1, wherein
$X_1$ is halogen, and
$X_2$ and $X_3$ are each hydrogen.

3. A compound of claim 2, wherein
$X_1$ is chlorine.

4. The compound of claim 3 of the formula

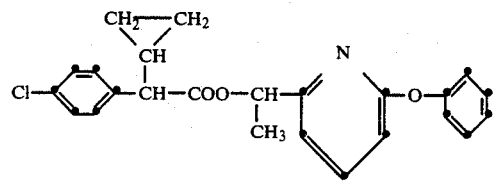

5. A pesticidal composition which contains an effective amount of a compound of claim 1, together with a carrier.

6. A method of controlling various pests on animals and plants, which method comprises applying thereto or to the locus thereof an effective amount of a compound of claim 1.

* * * * *